United States Patent [19]

Koch

[11] Patent Number: 4,609,354
[45] Date of Patent: Sep. 2, 1986

[54] ENOSSAL IMPLANT FOR SECURING A TIGHT-FITTING TOOTH REPLACEMENT

[75] Inventor: Werner L. Koch, Liebenau, Fed. Rep. of Germany

[73] Assignee: Implanto-Lock GmbH, Fed. Rep. of Germany

[21] Appl. No.: 720,564

[22] Filed: Apr. 5, 1985

[30] Foreign Application Priority Data

Apr. 11, 1984 [DE] Fed. Rep. of Germany ....... 3413578

[51] Int. Cl.$^4$ ................................................ A61C 8/00
[52] U.S. Cl. ..................................................... 433/173
[58] Field of Search .................. 29/667; 433/173, 174, 433/175, 176

[56] References Cited

U.S. PATENT DOCUMENTS 3,849,887 11/1974 Branin ................................... 433/173
4,314,396 2/1982 Nunlist et al. ......................... 29/447
4,499,646 2/1985 Allor et al. ............................ 29/447

Primary Examiner—Robert Peshock
Attorney, Agent, or Firm—Allegretti, Newitt, Witcoff & McAndrews, Ltd.

[57] ABSTRACT

An enossal implant for securing a tight-fitting tooth replacement having two parts which are to be connected with one another. One part, having a bore hole, is placed in the jawbone. The other part, comprising a peg which serves to hold the replacement tooth, is replaceably inserted in the hole. The diameter of the cylindrical external wall of the peg is dimensioned larger than the diameter of the bore hole so that the peg, at body temperature, is compressed within the bore hole, but at reduced temperature can be removed from the bore hole due to reduction in the external dimensions of the peg. Such a connection is simple to handle, cannot loosen, and is practically free of cavities so that no bacterial colonies can form in the implant.

10 Claims, 2 Drawing Figures

ENOSSAL IMPLANT FOR SECURING A TIGHT-FITTING TOOTH REPLACEMENT

The invention concerns an enossal implant for securing a tight-fitting tooth replacement comprising one part with a socket disposed in the bone, and a peg of larger size than the socket which carries the tooth. The peg is contracted by lowering its temperature to permit insertion in the socket, whereupon the peg, at body temperature, expands into tight contact with the socket.

An enossal implant of this type is disclosed in German patent specification 24 13 883. A threaded bore in the part which is to be inserted into the jawbone has a lining or sleeve with external threads of flexible material and internal threads. A threaded pin, which serves to secure the tight-fitting tooth replacement, is screwed into the sleeve, but the two parts are not in firm contact. The tooth-holding mechanism of a natural tooth is intended to be imitated by this plastic intermediary sleeve in the form of a threaded lining. Through the cooperating threads, the replacement and adjustment of the flexible threaded lining is possible.

This known implant fully and completely fulfills the demands for the imitation of the tooth-holding mechanism and adjustability. However, it has been shown that the threaded surfaces of the lining or sleeve can lead to infections. The cause for this lies in the fact that in use the forces between the threads diminish and spaces form in which bacteria can lodge, which can lead to inflammations.

The object of this invention is to provide an implant of the type described, in which no loosening occurs, and thus no bacterial colonies can form or inflammations arise.

The object is achieved by utilizing the principle that materials contract at low temperatures and expand at body temperature.

The invention departs from the principle of using threaded parts and instead provides a clamping or pressed fit between a peg and a corresponding bore hole. The dimension of the peg periphery or circumference is selected in connection with the thermal coefficient of the peg material so that at normal body temperature an adequate clamping fit is achieved. At the same time, the dimension is so selected, that upon reduction of temperature, the diameter of the peg is reduced to permit removal of the peg from the bore hole.

Proper reduction in the size of the peg through temperature reduction is possible, if the material used for the peg and the part which contains the bore hole have the same coefficient of thermal expansion, since only the peg is cooled. A rapid cooling must thereby take place in order to avoid a simultaneous cooling of the material containing the bore hole. Such a rapid cooling is possible with fluids which evaporate at body temperature.

According to a preferred form of the invention, the peg consists of a material, the thermal expansion coefficient of which is greater than that of the material which contains the bore hole. This insures that even if the part which contains the bore hole also becomes cooled, the diameters are different because of the differing thermal coefficients of expansion. Thus it is possible to remove the peg from the bore hole.

Metal is especially well-suited as a material for the peg and/or the part which contains the bore hole; however, a non-metallic substance, especially plastic, is also suitable. This is especially the case for the peg, so that, despite the disadvantages arising from the plastic which were stated above with respect to the state of the art, the use of plastic is possible.

The invention takes advantage of the fact that bonding forces work essentially laterally to the normal stress of the implant imposed by chewing forces. During chewing with a conventional implant, the traction forces exerted by the threads, and thereby the locking forces, diminish. In contrast, the holding forces produced by the construction of the invention are unimpaired.

To secure the peg, it is useful to make it as long as possible. On the other hand, increased length requires additional cooling, since the peg must be cooled to its end. This difficulty is avoided by putting an extension on the peg which is insulated from the peg proper. The lengthening of the peg held at body temperature with a side fitting, essentially contributes to a good mounting of the peg. By insulating the peg from the extension, cooling of the extension is avoided so that the temperature of the peg can be rapidly and sharply reduced. Thus a prompt loosening of the peg is possible. In this form of the invention, the peg itself serves as the element that holds, in an axial direction, the overall structure, consisting of peg and extension in the corresponding bore hole of the part which is inserted into the jawbone. The essentially superfluous forces from the extension are transferred into the part containing the bore hole. In accordance with this construction, it is possible to lengthen the peg for secure mounting, while dimensioning the diameter as specified by the invention only down to the area of the root of the peg, in which cooling poses no difficulties.

The bore hole, in which the extension of the peg rests, preferably has the same diameter as the bore hole for the peg. It can, however, also be smaller, for which, of course, an additional manufacturing step is required.

The extension must be coupled with the peg, and this is accomplished by a pin extending through a bore within the peg and the extension. To insulate the pin from the peg, an insulating sleeve or liner is provided in the bore hole of the peg. The pin protrudes above the top of the liner and terminates in means for securing the tight-fitting tooth replacement. In this manner, a large part of the force conducted from the tooth replacement into the bone traverses through the pin into the part of the implant which sits in the bone. The liner has on its upper end a radially-directed flange covering the upper edge of the peg. Instead of the flange, a separate insulating washer can be medially positioned.

The sleeve or liner extends into the part which is to be anchored in the jawbone and is closed at its lower end. The pin extends to the bottom of the sleeve but is not directly connected with the part of the implant to be anchored in the jawbone, and is thus thermally insulated from this part. Upon the cooling of the part which serves to secure the tooth replacement and the pin protruding from it, a draining of cold through the pin into the implant part resting in the jawbone is avoided.

The liner has a threaded stud extending from its bottom which is screwed into the extension. The liner also has internal threads at its lower end into which the pin is screwed. These members all form, together with the part which serves to secure the tooth replacement, the removable parts of the unit.

The extension of the peg preferably has a higher coefficient of elasticity than the peg. The stress peaks are thus reduced, and the moving of the extension in the bore hole is thereby facilitated.

Further details and advantages of the invention will be explained from the drawing, in which.

Figure 1:
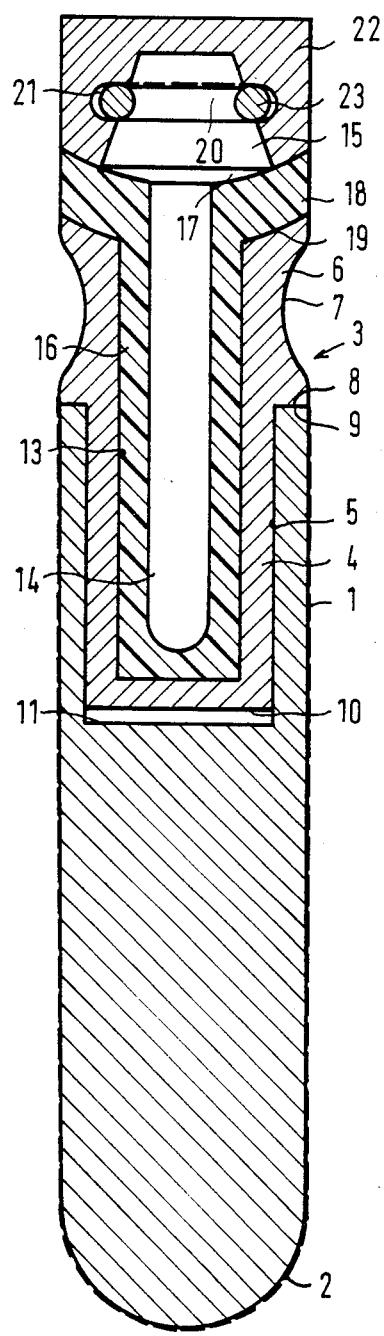
FIG. 1 is a partial section through an enossal implant constructed in accordance with one form of the invention.

The implant depicted in FIG. 1 has a part in the form of a shaft 1 which has a hemispherical end 2 which can be inserted into a cavity in a jawbone, and a part 3 which includes a cylindrical peg 4 for a press fit into a blind bore hole 5 in the upper end of shaft 1. On its upper end, the part 3 has a head 6 in which there is a lateral or circumferential constriction 7 which, in the installed implant, lies at the level of the gum or of the outlet from the same. The head 6 has a shoulder 8 on its underside which bears against the top edge 9 of the shaft 1. The lower end 10 of the peg 4 ends short of the base 11 of the bore hole 5.

The peg 4 consists of a material, the thermal coefficient of which is greater than that of the material of shaft 1. The diameter of the peg in a non-installed condition at body temperature is so much greater than the diameter of the bore hole, that a solid press fit is created when the peg is installed in the hole.

Another blind bore hole 13 is provided in head 6 and peg 4, which hole is lined with an intermediate layer in the form of a plastic sleeve 16. A cylindrical pin 14 terminates in the upper end in a frusto conical head spaced above head 6. An intermediate layer 16 of the flexible material, such as plastic, is disposed in the space. The underside of the cone 15 forms a contact surface 17 which rests on a flange 18 of the sleeve 16. The flange rests on the upper edge 19 of head 6. The contact surfaces 17 and 19 are cup-shaped. All surfaces of the sleeve 16 and the flange 18 of the flexible material are securely adhered to the contact surfaces of adjacent parts as by gluing or casting.

A circular groove 20 is located in the external conical surface of the head 15 opposite a groove 21 located in the complementary inner conical fitting surface of a fastening part or cap 22. An essentially U-shaped retaining spring 23 fits into the cooperating grooves 20 and 21, and the spring firmly connects both parts 15 and 22 with one another. The connection between head 15 and cap 22 is movement-free and can be easily loosened. Moreover, torsion forces are not transferred to pin 14, and thus the pin cannot be loosened.

In applying the implant in the jawbone, a recession or cavity, which is essentially complementary to shaft 1, is first of all cut, and shaft 1 is inserted. The bore hole 5 is closed with a plug similar to the part 3 which has a short head over which the gums are closed so that the shaft 1 can firmly heal in. Afterwards, the gums are perforated and the plug in the bore hole 5 is removed. The part 3 is cooled and then quickly inserted with its peg 4 into the bore hole 5. As soon as the temperature of the peg 4 rises to body temperature, a firm clamping or pressing connection exists between parts 1 and 3 of the implant. The mechanical properties of the flexible sleeve 16 and its flange 18 are selected corresponding to the values of the tooth-holding apparatus, the imitation of which is desired. When part 3 is thus fastened, the cone 15 protrudes freely out of the gums so that the fastening cap 22, which is in the meantime connected with a tooth replacement (not shown), can be set on it. The securing of the fastening cap 22, with the tooth replacement resting on it, takes place through lateral insertion of the retaining spring 23 which can be removed at any time for purposes of inspection or cleaning of the tooth replacement.

If it is desired to remove the part 3, the head 6 is cooled, for example, through spraying with a rapidly-evaporating fluid. This cools the peg, 4 thereby reducing its diameter so the peg 4 can be removed from the bore hole.

Figure 2:
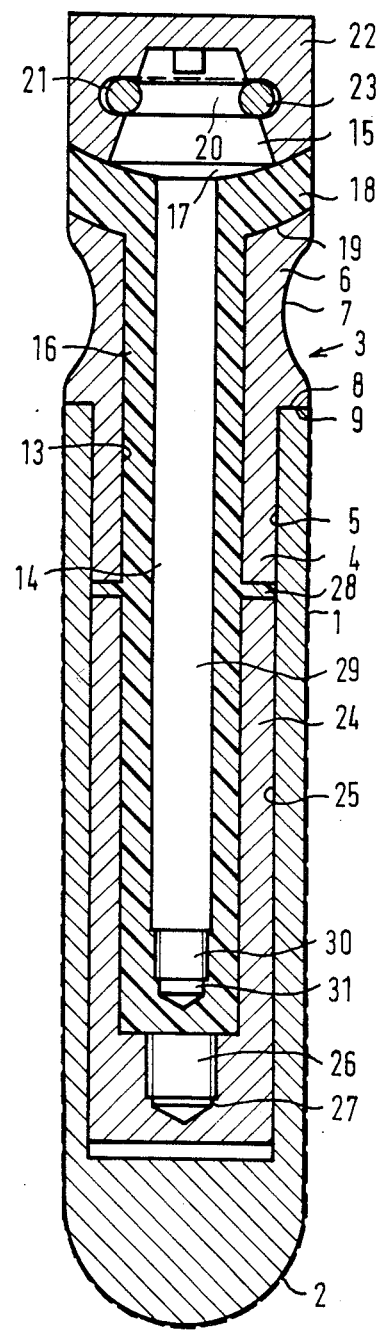
FIG. 2 is a similar view showing an alternative form of the invention.

FIG. 2 depicts an alternative form of the invention shown in FIG. 1. Corresponding parts are designated with the same reference numbers. The difference consists of the fact that an extension 24 of peg 4 is provided which slides into the correspondingly elongated bore hole 5 in shaft 1 at body temperature. The intermediate sleeve 16, formed as a liner, extends into a bore hole 13 of the extension 24, and is screwed by means of a threaded pin 26, extending from the bottom of the closed end of the sleeve into a threaded blind bore 27 in the bottom of the extension 24. Between the lower edge of the peg 4 and the opposed upper edge of the extension 24, there is a flange 28 comprising part of sleeve 16 which forms the liner. This consists of a material which conducts heat poorly (plastic, for example), and thus insulates both parts relative to the thermal conductivity.

An elongated pin 29 interconnects the peg 4 with its extension 24. The lower end 30 of pin 29 is threaded and screwed into a threaded blind end bore 31 in the bottom of extension 24.

The peg 4, its extension 24, pin 29, sleeve 15, and component parts, form a unit which can be inserted into the bore hole 5 of the shaft 1, by cooling the peg 4 as described in connection with FIG. 1.

The basic idea of the invention in connecting two parts of implants through thermal expansion and contraction, is also applicable for the connection between the part which serves to secure the tooth replacement and the tooth replacement itself. It is also applicable to the connection of parts of the tooth replacement.

I claim:

1. An enossal implant for securing a tight-fitting tooth replacement in a cavity in the bone, comprising
   a shaft for insertion in said cavity,
      said shaft having a cylindrical blind bore in the upper end thereof,
   a peg to one end of which said tooth is anchored,
      said peg being larger in diameter than said blind bore and being made from a material which, at low temperatures, contracts sufficiently to permit insertion into or removal from said blind bore, and
   an extension from the other end of said peg disposed within said blind bore and an insulating annular disc having low conductivity interposed between said peg and said extension, the cross-section of said extension being smaller than said blind bore at room temperature, and a central pin interconnecting said peg and said extension.

2. The implant of claim 1 in which the portion of said blind bore encircling said extension has the same diameter as the portion encircling said peg.

3. The implant of claim 1 in which said peg has an axial bore lined with a sleeve having low thermal conductivity, said sleeve surrounding said pin.

4. The implant of claim 3 in which said pin protrudes from said one end of said peg and carries a head to which a replacement tooth is secured.

5. The implant of claim 4 in which said insulating disc constitutes a flange of said liner and said liner also includes a second flange between the top edge of said peg and the underside of said head.

6. The implant of claim 3 in which said sleeve has a closed bottom terminating in a threaded socket and said lower end of said pin is screwed into said socket.

7. The implant of claim 1 in which said extension has a higher coefficient of elasticity than the peg.

8. An enossal implant for securing a tight-fitting tooth replacement in a cavity in the bone comprising a shaft for insertion in said cavity, said shaft having a bore in the upper end thereof, a peg disposed in said bore to one end of which said tooth is anchored, said peg at human body temperature having an external diameter larger than the internal diameter of said bore and at reduced temperature having an external diameter smaller than the internal diameter of said bore, said peg being made from a material having a coefficient of thermal expansion greater than the shaft materal surrounding the bore, whereby said peg and the tooth can be removed from the bore.

9. The implant of claim 8 in which said peg material is plastic.

10. The implant of claim 8 in which said peg and said bores are cylindrical.

* * * * *